United States Patent [19]

Nash

[11] 4,316,775
[45] Feb. 23, 1982

[54] TREATMENT OF WASTE STREAM FROM ADIPIC ACID PRODUCTION

[75] Inventor: William D. Nash, Odessa, Tex.

[73] Assignee: El Paso Products Company, Odessa, Tex.

[21] Appl. No.: 204,506

[22] Filed: Nov. 6, 1980

[51] Int. Cl.³ .............................................. B01D 3/12
[52] U.S. Cl. ...................................... 203/43; 203/72; 203/89; 562/593
[58] Field of Search .................... 562/593; 203/73, 77, 203/80, 91, 89, 43–46, 72, 75, 78, 82, 84; 159/5, 6 W, 6 WH

[56] References Cited

FOREIGN PATENT DOCUMENTS 1191357  4/1965  Fed. Rep. of Germany ........ 203/89

*Primary Examiner*—Frank Sever
*Attorney, Agent, or Firm*—Depaoli & O'Brien

[57] ABSTRACT

This invention provides a process for improving the recovery of byproducts associated with the isolation of $C_4$–$C_6$ dicarboxylic acids contained in a waste byproduct stream, wherein the byproduct stream is derived from an adipic acid manufacturing operation involving nitric acid oxidation of a cyclohexanone/cyclohexanol feedstream.

The main byproducts which are isolated are high purity dimethyl succinate, dimethyl glutarate and dimethyl adipate. Monomethyl esters of these dicarboxylic acids are recovered and recycled in the process.

3 Claims, 1 Drawing Figure

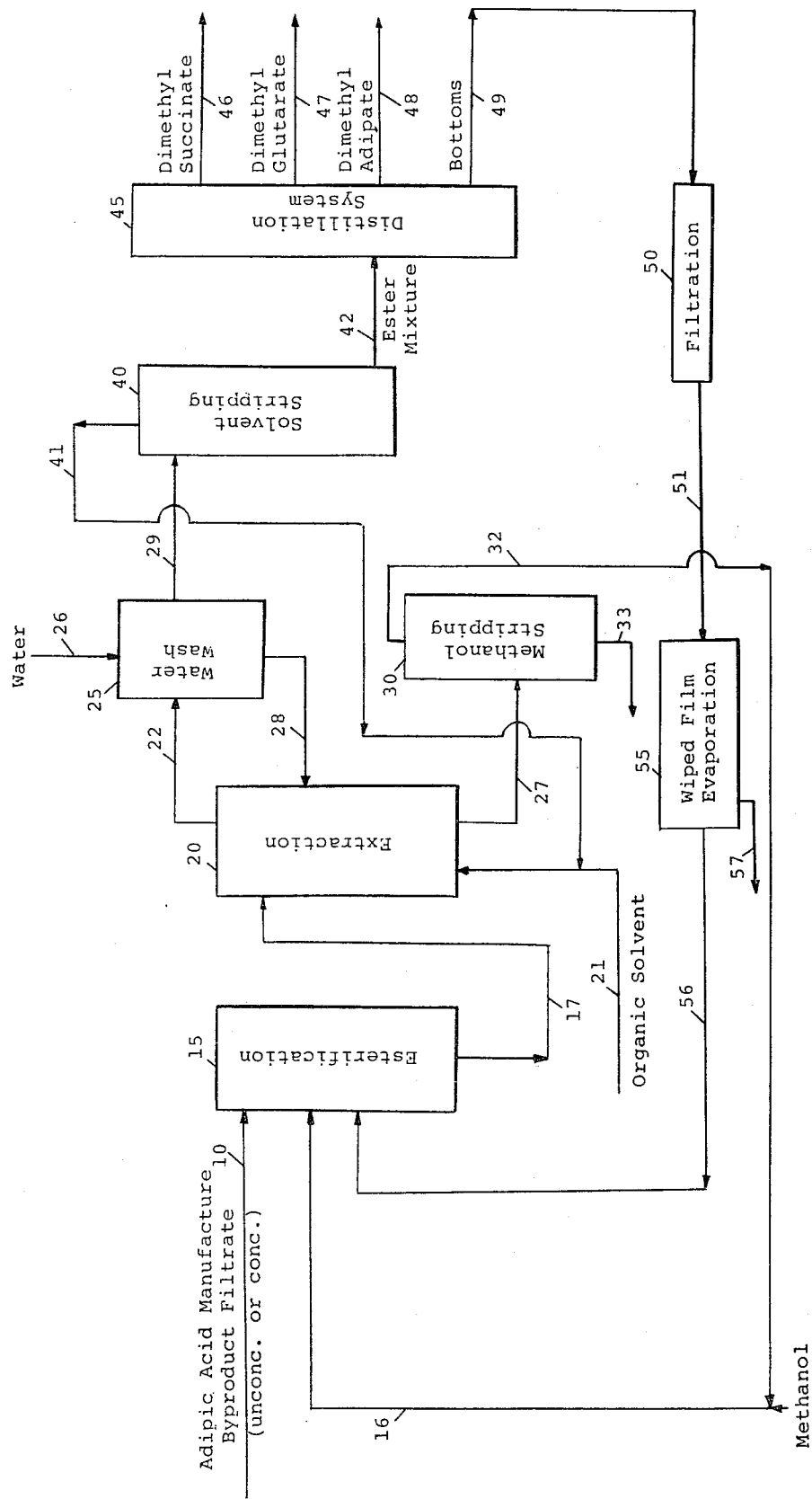

TREATMENT OF WASTE STREAM FROM ADIPIC ACID PRODUCTION

BACKGROUND OF THE INVENTION

Commercial methods for producing dicarboxylic acids generally involve oxidizing naphthenes, cycloaliphatic ketones or cycloaliphatic alcohols with nitric acid in the presence of metal oxidation catalysts.

In the case of adipic acid, specific feed materials such as cyclohexane, cyclohexanol and/or cyclohexanone in admixture with nitric acid are heated at about 40°–140° C. in the presence of a catalyst. The resultant oxidation reaction product comprises adipic acid together with small amounts of monocarboxylic acids and dicarboxylic acids and other organic components in admixture with nitric acid and catalyst components. A substantial quantity of the adipic acid product is recovered by cooling the solution and filtering off the crystallized adipic acid. Oxidation methods of adipic acid production are described in U.S. Pat. Nos. 2,439,513; 2,557,281; 2,719,566; 2,840,607; 2,971,010; 3,338,959; and references cited therein.

In a process involving nitric acid oxidation of cyclohexanone and/or cyclohexanol, economically significant amounts of succinic acid and glutaric acid are formed as byproducts in admixture with the adipic acid. After the major portion of the adipic acid is separated by crystallization and filtration, the filtrate mother liquor contains some adipic acid, as well as succinic acid, glutaric acid, nitric acid and metal catalyst values.

Usually this filtrate has been treated as a waste stream. Because of environmental and economic considerations, there has been continuing research effort to develop methods for recovering the valuable and reusable organic and inorganic components of the said filtrate waste byproduct stream.

U.S. Pat. No. 3,726,888 describes a process for the separation and recovery of the components contained in the filtrate waste byproduct stream of an adipic acid manufacturing plant. The filtrate stream comprises a mixture of adipic acid, glutaric acid, succinic acid, nitric acid and metal catalyst values. The separation and recovery process involves contacting the filtrate with alkanol, and extracting with a water-immiscible organic solvent to provide an organic phase containing the formed esters, and to provide an aqueous phase containing the nitric acid and metal catalyst values. Each of the phases is fractionated to separate the mixtures into useful components.

U.S. Pat. Nos. 4,058,555; 4,076,948 and 4,082,788 describe processing improvements which are adapted to overcome some of the difficulties characteristic of the byproduct separation and recovery technology disclosed in the above recited U.S. Pat. No. 3,726,888.

One of the several problems associated with the production of esters of $C_4$–$C_6$ carboxylic acid components (i.e., those acid components contained in the filtrate byproduct stream derived from adipic acid manufacture) is the accumulation of a residual bottoms fraction which results from the fractional distillation procedure for the recovery of refined diesters of succinic acid, glutaric acid and adipic acid.

If the residual bottoms fraction is recycled to the esterification step in the ester production and recovery process, the heavy organic components of the said residual bottoms fraction cause fouling of the esterification and extraction equipment employed in the process. For this reason the described residual bottoms fraction normally is disposed of as a waste stream by burning or dumping.

There remains a need for new technology to improve economic and environmental aspects of adipic acid production by increased conversion of the filtrate waste stream into useful products.

Accordingly, it is a main object of this invention to improve the efficiency of an adipic acid manufacturing operation by recovery of byproduct values.

It is another object of this invention to provide a process for improving the material balance associated with the separation and recovery of $C_4$–$C_6$ dicarboxylic acids contained in a filtrate byproduct stream derived from an adipic acid manufacturing operation involving nitric acid oxidation of cyclohexanone and/or cyclohexanol.

It is a further object of this invention to recover $C_4$–$C_6$ byproducts from an adipic acid manufacturing operation involving nitric acid oxidation of cyclohexanone and/or cyclohexanol, wherein the recovered $C_4$–$C_6$ byproducts are in the form of high purity dicarboxylic acid diesters.

Other objects and advantages of the present invention shall become apparent from the accompanying description and illustrated data.

DESCRIPTION OF THE INVENTION

As noted previously, in the oxidation of cyclohexanone and/or cyclohexanol with nitric acid in the presence of a metal oxidation catalyst, the resulting oxidation product solution is processed for recovery of the bulk of the desired adipic acid by crystallization and filtration. The acidic mother liquor (i.e., the aqueous filtrate byproduct stream) contains quantities of monobasic and dibasic carboxylic acids as well as nitric acid and metal catalyst values. These filtrate components are sufficiently valuable to invite the application of recovery procedures, particularly in view of the environmental protection ramifications.

A typical filtrate byproduct stream nominally corresponds to the following weight percent composition:

| Component | Amount |
|---|---|
| Succinic acid | 3–10% |
| Glutaric acid | 8–35% |
| Adipic acid | 3–6% |
| Nitric acid | 6–20% |
| Catalyst | 1–3% |
| Water | Balance |

The catalyst values contained in the filtrate are those which are conventionally employed in cyclohexanone/cyclohexanol oxidation procedures, such as copper, vanadium, and the like.

The present invention process is adapted to improve the material balance associated with the separation and recovery of $C_4$–$C_6$ dicarboxylic acids which are contained in the said filtrate byproduct stream of an adipic acid manufacturing operation. The invention process is particularly applicable to a $C_4$–$C_6$ dicarboxylic acid separation and recovery method which proceeds via an intermediate ester formation step.

Thus, one or more objects of the present invention are accomplished by the provision of an improved process for producing methyl esters of $C_4$–$C_6$ carboxylic acid components contained in an aqueous filtrate, which filtrate is a waste byproduct stream derived from the production of adipic acid by nitric acid oxidation of cyclohexanone/cyclohexanol, wherein the said process comprises the steps of admixing the aqueous filtrate byproduct stream with methanol and heating the admixture to form methyl esters of the $C_4$–$C_6$ carboxylic acid components, extracting the methyl ester components by contacting the esterification medium with a water-immiscible organic solvent, and separating the immiscible organic solvent phase and aqueous phase, the improvement which comprises (1) distilling the said organic solvent phase to yield dimethyl esters of succinic acid, glutaric acid and adipic acid, and a distillation bottoms fraction; (2) subjecting the said bottoms fraction to wiped film evaporation to provide a vapor condensate fraction and a residual heavy end fraction; and (3) recycling the said condensate fraction to the esterification step of the process.

With reference to the improvement aspects of the invention process, in step (1) as indicated in the above definition, the recovered organic solvent phase is fractionally distilled to isolate refined dimethyl esters of succinic acid, glutaric acid and adipic acid. The dimethyl esters may be recovered either as a mixture of esters or as individual species.

The fractional distillation system can comprise a single distillation column or a series of distillation columns. For example, the organic solvent phase containing dimethyl esters can be passed through a solvent stripping unit to separate the solvent from the admixture of dimethyl ester components. The overhead solvent fraction can be recycled to the extraction system. The solvent stripping unit preferably is equipped with a side draw to remove esters of monobasic acids and other light ends which are present in the solvent phase.

The crude dimethyl ester fraction, stripped of organic solvent and light ends, can be fed into a first distillation unit which is controlled to distill the lowest boiling ester components, e.g., dimethyl oxalate. Simultaneously, dimethyl succinate is withdrawn from the side of the column. The residual higher boiling ester fraction is recovered and passed into a second distillation unit, wherein dimethyl glutarate is distilled overhead and dimethyl adipate is separated as a side draw, leaving a distillation bottoms residuum. Nominally the residual bottoms fraction contains succinic acid, glutaric acid, adipic acid, and monomethyl esters thereof, in addition to other components such as succinic and glutaric anhydrides and relatively nonvolatile tars and resins. Overall processing efficiency is improved if the distillation bottoms fraction is filtered before it is entered into the wiped film evaporation unit.

In step (2) of the above described process embodiment, the distillation bottoms fraction is entered into a wiped film evaporation unit to effect a flash separation between volatile and nonvolatile components. The wiped film evaporation unit normally will be operated at a temperature in the range between about 130°–200° C. and at a subatmospheric pressure in the range between about 15–150 mm Hg. On the average, the distillation bottoms fraction which is subjected to wiped film evaporation will yield between about 60–90 weight percent of vapor condensate fraction and between about 10–30 weight percent of residual heavy end fraction, based on the initial weight of the distillation bottoms feedstream.

As noted previously, the vapor condensate fraction recovered from the wiped film evaporation unit is recycled to the esterification stage of the process. The residual heavy end fraction is removed from the system as a waste byproduct stream. This fraction represents only a minor quantity of heavy organic material and is readily disposable by burning, and the like.

The vapor condensate fraction that is recycled to the esterification stage of the process consists substantially of monomethyl esters of succinic acid, glutaric acid and adipic acid. The condensate fraction also contains minor quantities of these carboxylic acids in the free form, and residual quantities of dimethyl esters of the same acids, particularly dimethyl adipate.

Wipe film evaporators are available as manufactured equipment under various trademarks. Artisan Industries markets a series of Rototherm evaporators which vary in size from $\frac{1}{4}$ to 100 square feet of heat transfer area. A heat flux as high as 75,000 BTU per hour per square foot can be achieved.

A wipe film evaporator operates on a turbulent film principle. Feed stream entering a unit is thrown by centrifugal force against a heated process wall to form a turbulent film between the wall and rotor blade edges. Feed in process is exposed to boiling temperatures for only several seconds.

The practice of the present invention as a continuous process can be better understood by reference to the accompanying drawing which is illustrated as a flow diagram.

In the drawing, a filtrate stream is fed through line 10 into Esterification unit 15. Methanol is fed into Esterification unit 15 via line 16, and the esterification reaction is conducted at a temperature of 70° C. for a period of about 15–°minutes to form methyl esters of $C_4$–$C_6$ carboxylic acids.

The esterification reaction medium is withdrawn continuously from esterification unit 15 through line 17 and introduced into Extraction unit 20. An organic solvent (e.g., benzene) is fed countercurrently into Extraction unit 20 by means of line 21. The extraction cycle is conducted at a temperature of 70° C. for a contact time of about 5–10 minutes.

The organic solvent phase is recovered from Extraction unit 20 and passed through line 22 into Water Wash unit 25, and there it is contacted countercurrently with water which is fed through line 26 into Water Wash unit 25.

The aqueous phase is recovered from Extraction unit 20 and passed through line 27 into Methanol Stripping unit 30. The stripped methanol from unit 30 is cycled Esterification unit 15 through line 32, and the concentrated aqueous nitric acid solution and the catalyst values contained therein is recycled from unit 30 to the adipic acid production unit through line 33.

The spent water wash effluent from Water Wash unit 25 is recycled through line 28 to Extraction unit 20. The water washed organic solvent stream is recovered from Water Wash unit 25 and passed through line 29 into Solvent Stripping unit 40. The stripped organic solvent from unit 40 is recycled to Extraction unit 20 via line 41.

A refined mixed dimethyl ester fraction is withdrawn from Solvent Stripping unit 40 through line 42, and charged to Distillation System 45. Lines 46, 47 and 48 are employed to withdrawn dimethyl succinate, dimethyl glutarate and dimethyl adipate, respectively. Distillation System 45 can consist of a single fractional distillation unit, or it can consist of a series of two or more distillation units as previously described hereinabove.

The distillation bottoms fraction is withdrawn from Distillation System 45 via line 49 and passed through Filtration Unit 50. The filtered bottoms stream is charged to Wiped Film Evaporation unit 55 through line 51. Evaporation unit 55 is operated at a temperature of 130°–180° C. and a reduced pressure of 10–100 mm Hg. A typical volume capacity for a plant scale evaporation unit 55 is about 500 pounds per hour.

With reference to other aspects of the invention process practice, in one preferred embodiment this invention contemplates an improved process for producing methyl esters of $C_4$–$C_6$ carboxylic acid components contained in an aqueous filtrate, which filtrate is a waste byproduct stream derived from this production of adipic acid by nitric acid oxidation of cyclohexanone/cyclohexanol, the improvement which comprises the steps of (1) concentrating the volume of the aqueous filtrate medium by the partial removal of water and the volatile components which co-distill with water to provide a concentrate solution; (2) admixing the concentrate solution with methanol, and heating the solution at a temperature between about 60°–90° C. to form methyl esters of the $C_4$–$C_6$ carboxylic acid components; (3) extracting the methyl ester components by contacting the esterification medium with a water-immiscible organic solvent at a temperature between about 40°–90° C.; (4) separating the immiscible organic solvent phase and aqueous phase; (5) fractionally distilling the organic solvent phase from step (4) to yield a mixed dimethyl ester fraction, and a distillation bottoms fraction; (6) subjecting the said bottoms fraction to wiped film evaporation to provide a vapor condensate fraction and a residual heavy end fraction; and (7) recycling the said condensate fraction to the esterification step of the process.

In another preferred embodiment, this invention contemplates an improved method for producing dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60°–90° C. to form methyl esters of the $C_4$–$C_6$ carboxylic acid components; (3) extracting the methyl ester components by contacting the esterification medium with a water-immiscible organic solvent at a temperature between about 40°–90° C.; (4) separating the immiscible organic solvent phase and aqueous phase; (5) concentrating the aqueous phase from step (4) by distillation to provide an aqueous concentrate containing nitric acid and metal catalyst values; (6) fractionally distilling the organic solvent phase from step (4) to yield dimethyl esters of succinic acid, glutaric acid and adipic acid, and a distillation bottoms fraction; (6) subjecting the said bottoms fraction to wiped film evaporation to provide a vapor condensate fraction and a residual heavy end fraction; and (7) recycling the said condensate fraction to the esterification step of the process.

In the two preferred embodiments described above, a particularly important aspect is the step (1) concentration of the volume of the aqueous filtrate medium by the removal of water and nitric acid, and other volatile components which co-distill with water. The volatile components which co-distill with the water and nitric acid include butyric acid, valeric acid and caproic acid.

Several advantages derive from the step (1) concentration of the aqueous filtrate byproduct stream.

First, the reduced volume of the filtrate medium permits the use of smaller capacity equipment for the subsequent esterification and extraction steps of the process.

Second, the reduced proportion of water in the filtrate concentrate solution causes a favorable equilibrium shift toward ester formation in the step (2) esterification reaction.

Third, the removal of monobasic acids during the step (1) concentration of the filtrate byproduct stream facilitates the production and recovery of dimethyl esters having improved color and odor specifications.

Fourth, the removal of nitric acid during the step (1) concentration of the filtrate byproduct stream has the important advantage of reducing the level of methyl nitrite and methyl nitrate byproduct formation during the step (2) esterification. The formation of these byproducts is primarily a function of the nitric acid concentration. These byproducts are undesirable because they cause the loss of both methanol and nitric acid. Further, these byproducts tend to be unstable and represent a potential explosion hazard. They must be purged periodically from the process system.

Fifth, the recovery of nitric acid during the step (1) concentration phase permits a highly efficient recycle of the said nitric acid to the cyclohexanone/cyclohexanol oxidation system.

With reference to step (2) of the two preferred embodiments, a unique feature of the esterification reaction is the rate efficiency with which equilibrium is achieved between the esterified and unesterified dicarboxylic acid components, even in the presence of a highly dilute aqueous nitric acid solution. The efficiency of the step (2) esterification reaction is attributable to a combination of controlling factors, such as an elevated reaction temperature, a high proportion of methanol relative to a low proportion of water, the absence of interfering byproduct components (e.g., monocarboxylic acids), and the like.

The step (2) esterification reaction time on the average will vary in the range between about 5–25 minutes, depending in part on the temperature maintained in the esterification zone.

In a similar manner, the combination of delimiting parameters of the step (3) extraction stage of the two preferred embodiments provides processing advantages. Hence, an extraction temperature in the range between about 40° C.–90° C. has the beneficial effect of accelerating the additional conversion of free carboxylic acids to methyl ester derivatives. Substantially complete transfer of dimethyl esters into the organic solvent phase is achieved during the step (3) extraction period. This efficient extraction of dimethyl esters by the organic solvent is readily accomplished within a phase contact period between about 2–20 minutes.

The quantity of water-immiscible organic solvent employed in the step (3) extraction stage usually will vary in the range between about 0.5–2 volumes per volume of esterification medium being extracted, and on the average will approximate a volume ratio of 1:1.

A preferred type of water-immiscible organic solvent is one selected from aromatic hydrocarbons, halogenated aliphatic hydrocarbons and halogenated aromatic hydrocarbons. Particularly preferred species include benzene, toluene, xylene, ethylbenzene, chloroform, o-dichlorobenzene, and the like.

Because of the elevated up to 90° C. temperature employed during the esterification and extraction steps of the two preferred embodiments, equipment is employed which is adapted for 15-100 psi reaction systems.

At the end of the step (3) extraction period, the immiscible organic solvent and aqueous phases are separated and individually recovered in step (4) for subsequent manipulative procedures.

In a particularly preferred procedure, the recovered organic solvent phase is contacted with wash water in a manner sufficient to remove substantially all of the methanol and residual nitric acid components present in the organic solvent phase, and to reduce the free carboxylic acids and monomethyl esters of dicarboxylic acids content of the organic solvent phase. The water washing step facilitates the subsequent recovery of high quality diester byproducts.

The said organic solvent phase from step (4) is distilled to strip the solvent medium, and yield a refined mixed dimethyl ester fraction. The said ester mixture can be employed directly to prepare high molecular weight esters applicable as plasticizers for polyvinyl chlorides. Alternatively, the ester mixture can be further fractionated to yield pure dimethyl succinate, dimethyl glutarate and dimethyl adipate, respectively. If desired, the dimethyl esters can be hydrolyzed to the corresponding high purity acids.

With respect to the aqueous phase which is separated and recovered in step (4) after the step (3) extraction operation, the said aqueous phase is subjected to concentration in vacuo to remove the dissolved methanol content and to provide an aqueous concentrate solution containing nitric acid and copper/vanadium type metal values. The said aqueous concentrate solution is suitable for recycle to the cyclohexanone/cyclohexanol oxidation system.

The two preferred embodiments described above can be conducted as a continuous process. The two process embodiments can be operated in accordance with the flow diagram illustrated in the drawing, except that a *concentrated* filtrate is fed through line 10.

Another important advantage of the present invention processing embodiments derives from the wiped film evaporation method of partitioning the distillation system bottoms residuum into a vapor condensate fraction and a heavy end fraction. The wiped film evaporation procedure permits the throughput of a large volume of feed material with an efficient high yield recovery of vapor condensate suitable for recycle to the esterification step of the invention process. The relatively low temperature and short heating period to which the feed material is subjected in the wiped film evaporation zone minimizes side reactions which produce anhydrides, decomposition products, and the like.

The following example is further illustrative of the present invention. The reactants and processing conditions are presented as being typical, and various modifications can be derived in view of the foregoing disclosure within the scope of the invention.

EXAMPLE

This example illustrates the present invention process in which a concentrated adipic acid byproduct mother liquor is employed as the starting feedstream.

A filtrate byproduct stream (i.e., waste mother liquor) from an adipic acid manufacturing plant is distilled at subatmospheric pressure to reduce the water and nitric acid contents of the mixture and provide a concentrate solution.

The concentrate solution contains about 70 weight percent of adipic, glutaric and succinic acids. The other main components comprise about 5 weight percent nitric acid, 20 weight percent water, and about 1.0 weight percent copper and 500 ppm of vanadium.

A mixture of esterification reactants is prepared which has the following composition:

|  | Grams |
| --- | --- |
| Filtrate concentrate | 4846 |
| Methanol | 3368 |
| Nitric acid, 70% | 301 |
| Residual bottoms | 2536 |

The residual bottoms material is the fraction which is recovered from the fractional distillation system as illustrated in the drawing. The fraction contains monomethyl esters of succinic acid, glutaric acid and adipic acid, and additionally contains some nonvolatile oils and resins. For comparative purposes, the residual bottoms material being employed is not subjected to wiped film evaporation in accordance with the present invention process.

The esterification reaction mixture indicated above is stirred for one hour at 60° C. The resultant product mixture is fed into a glass extraction column which is packed with porcelain saddles.

The extraction column contains a 36 inch packed section. The column is thermostated at 60° C. and operates at a pressure of about 15 psig. The esterification feed is entered continuously into the extraction column at a point six inches below the top of the packed section. Benzene is fed continuously to the bottom of the extraction column, and water is fed continuously to the top of the extraction column. The function of the water is to wash methanol, nitric acid and catalyst values from the benzene phase during the extraction operation.

The volume ratio of benzene to esterification feed in the extraction volumn is 1:1.5, and the contact time between the two phases is about 10 minutes.

During the extraction operation, the extraction column packing becomes fouled with a deposit of black material. Subsequently, this material is found to be insoluble in each of water, benzene and methanol.

The benzene phase is recovered, and distilled to a pot temperature of 175° C. at a pressure of 70 mm of mercury. The distillate product is substantially dimethyl esters of adipic acid, glutaric acid and succinic acid.

The distillation residual bottoms material is recovered, and in accordance with the present invention process is fed continuously into a commercial Rototherm wipe film evaporator (Artisan Industries) which has a ¼ square foot heat transfer area.

The inside evaporator temperature is 170° C. and the overhead temperature is 152° C., at a system pressure of 18 mm Hg. The feed rate of bottoms material is 26.5 grams per minute.

About 79 weight % of the original feed material is recovered as overhead product. The overhead product consists of 5.7 wt. % of dimethyl glutarate, 65.6 wt. % of dimethyl adipate, 7.3 wt. % of monomethyl glutarate, 11.9 wt. % of monomethyl adipate, 2.2 wt. % of other volatile components, and 7.4 wt. % of nonvolatile material.

The overhead product is then recycled to the esterification step of the process, and esterification and subsequent extraction procedures are conducted in the same manner as described above. During the extraction operation, there is no deposit of black material as noted in the operation of the earlier extraction procedure.

The aqueous phase recovered from the extraction operation is concentrated in a methanol stripping unit and recycled to the primary cyclohexanone/cyclohexanol oxidation system. The adipic acid produced after the recycle of the concentrate aqueous catalyst solution is within specifications. If the same process is repeated, except that the wiped film evaporation step of the present invention is excluded, then the adipic acid which is produced in the primary cyclohexanone/cyclohexanol oxidation system does not meet color and other product specifications.

What is claimed is:

1. In a process for producing methyl esters of $C_4$–$C_6$ carboxylic acid components contained in an aqueous filtrate, which filtrate is a waste byproduct stream derived from this production of adipic acid by nitric acid oxidation of cyclohexanone/cyclohexanol, the improvement which comprises the steps of (1) concentrating the volume of the aqueous filtrate medium by the partial removal of water and the volatile components which co-distill with water to provide a concentrate solution; (2) admixing the concentrate solution with methanol, and heating the solution at a temperature between about 60°–90° C. to form methyl esters of the $C_4$–$C_6$ carboxylic acid components; (3) extracting the methyl ester components by contacting the esterification medium with a water-immiscible organic solvent at a temperature between about 40°–90° C.; (4) separating the immiscible organic solvent phase and aqueous phase; (5) fractionally distilling the organic solvent phase from step (4) to yield a mixed dimethyl ester fraction, and a distillation bottoms fraction, (6) subjecting the said bottoms fraction to wiped film evaporation to provide a vapor condensate fraction and a residual heavy end fraction; and (7) recycling the said condensate fraction to the esterification step of the process.

2. In a method for producing dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60°–90° C. to form methyl esters of the $C_4$–$C_6$ carboxylic acid components; (3) extracting the methyl ester components by contacting the esterification medium with a water-immiscible organic solvent at a temperature between about 40°–90° C.; (4) separating the immiscible organic solvent phase and aqueous phase; (5) concentrating the aqueous phase from step (4) by distillation to provide an aqueous concentrate containing nitric acid and metal catalyst values; (6) fractionally distilling the organic solvent phase from step (4) to yield dimethyl esters of succinic acid, glutaric acid and adipic acid, and a distillation bottoms fraction; (6) subjecting the said bottoms fraction to wiped film evaporation to provide a vapor condensate fraction and a residual heavy end fraction; and (7) recycling the said condensate fraction to the esterification step of the process.

3. A process in accordance with claim 2 wherein the aqueous concentrate provided by step (5) is recycled to the primary cyclohexanone/cyclohexanol oxidation stage of the process.

* * * * *

UNITED STATES PATENT OFFICE
CERTIFICATE OF CORRECTION

Patent No. 4,316,775      Dated February 23, 1982

Inventor(s) William D. Nash

It is certified that error appears in the above-identified patent and that said Letters Patent are hereby corrected as shown below:

Column 4, line 33, "15-°" should be --15-20--.

Column 4, line 63, "withdrawn" should be --withdraw--.

Signed and Sealed this

Twenty-second Day of June 1982

[SEAL]

Attest:

GERALD J. MOSSINGHOFF

*Attesting Officer*     *Commissioner of Patents and Trademarks*